(12) United States Patent
Aubert et al.

(10) Patent No.: US 11,641,917 B2
(45) Date of Patent: May 9, 2023

(54) MULTI-DIFFUSION-ORIFICE AEROSOL DEVICE FOR DRY-WASHING THE HAIR

(71) Applicant: L'OREAL, Paris (FR)

(72) Inventors: Lionel Aubert, Asnieres sur Oise (FR); Jonathan Gawtrey, Boulogne (FR); Nathalie Beau, Eragny-sur-Oise (FR); Nadia Smail, Vernouillet (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/888,013

(22) PCT Filed: Apr. 30, 2014

(86) PCT No.: PCT/EP2014/058894
§ 371 (c)(1),
(2) Date: Oct. 29, 2015

(87) PCT Pub. No.: WO2014/177647
PCT Pub. Date: Nov. 6, 2014

(65) Prior Publication Data
US 2016/0100667 A1 Apr. 14, 2016

(30) Foreign Application Priority Data
Apr. 30, 2013 (FR) ...................... 1354012

(51) Int. Cl.
*A61K 8/34* (2006.01)
*A61K 8/49* (2006.01)
(Continued)

(52) U.S. Cl.
CPC .............. *A45D 19/02* (2013.01); *A61K 8/046* (2013.01); *A61K 8/19* (2013.01); *A61K 8/31* (2013.01);
(Continued)

(58) Field of Classification Search
USPC ....... 239/333, 337, 463, 491, 492, 504, 543, 239/544, 548, 552, 556, 557, 558, 565,
(Continued)

(56) References Cited

U.S. PATENT DOCUMENTS

| 2,047,398 A | 7/1936 | Voss et al. |
| 2,102,113 A | 12/1937 | Djordjevitch |

(Continued)

FOREIGN PATENT DOCUMENTS

| DE | 2330956 A1 | 1/1974 |
| DE | 10 2005 025 016 A1 | 12/2005 |

(Continued)

OTHER PUBLICATIONS

Oscar Blandi. http://www.skinstore.com/p-6885-oscar-blandi-pronto-dry-shampoo-spray.aspx. Published Jun. 13, 2011.*
(Continued)

*Primary Examiner* — Nicole P Babson
*Assistant Examiner* — Lori K Mattison
(74) *Attorney, Agent, or Firm* — The Marbury Law Group, PLLC (57) ABSTRACT

The present invention relates to an aerosol device including: —a container containing: —one or more propellants, and—a composition including one or more sebum-absorbing powders with a sebum uptake of greater than or equal to 35 ml/100 g, the propellant(s) possibly being present in the composition or, in the container, separate from the composition, —an aerosol device for dispensing the said aerosol composition, including a diffuser equipped with at least two, and better three, spray orifices (22). The invention also relates to a process for the dry-washing and cosmetic treatment of keratin materials, including a step of applying to the hair the cosmetic composition, sprayed from the particular aerosol device.

14 Claims, 1 Drawing Sheet

(51) Int. Cl.
<table>
<tr><td>B05B 1/14</td><td>(2006.01)</td></tr>
<tr><td>A61Q 5/02</td><td>(2006.01)</td></tr>
<tr><td>A45D 19/02</td><td>(2006.01)</td></tr>
<tr><td>A61K 8/73</td><td>(2006.01)</td></tr>
<tr><td>A61K 8/04</td><td>(2006.01)</td></tr>
<tr><td>A61K 8/19</td><td>(2006.01)</td></tr>
<tr><td>B65D 83/14</td><td>(2006.01)</td></tr>
<tr><td>A61K 8/31</td><td>(2006.01)</td></tr>
<tr><td>A61K 8/37</td><td>(2006.01)</td></tr>
<tr><td>A61K 8/891</td><td>(2006.01)</td></tr>
<tr><td>A61K 8/892</td><td>(2006.01)</td></tr>
<tr><td>A61K 8/96</td><td>(2006.01)</td></tr>
<tr><td>B65D 83/28</td><td>(2006.01)</td></tr>
<tr><td>B65D 83/44</td><td>(2006.01)</td></tr>
<tr><td>B65D 83/20</td><td>(2006.01)</td></tr>
<tr><td>A45D 19/00</td><td>(2006.01)</td></tr>
</table>

(52) U.S. Cl.
CPC .......... *A61K 8/34* (2013.01); *A61K 8/37* (2013.01); *A61K 8/4973* (2013.01); *A61K 8/732* (2013.01); *A61K 8/891* (2013.01); *A61K 8/892* (2013.01); *A61K 8/965* (2013.01); *A61Q 5/02* (2013.01); *B65D 83/28* (2013.01); *B65D 83/44* (2013.01); *B65D 83/753* (2013.01); *A45D 19/005* (2021.01); *A61K 2800/31* (2013.01); *A61K 2800/87* (2013.01); *B05B 1/14* (2013.01); *B65D 83/206* (2013.01)

(58) Field of Classification Search
USPC .................................. 239/566, 567, 650, 654
See application file for complete search history.

(56) References Cited

U.S. PATENT DOCUMENTS

| | | | |
|---|---|---|---|
| 2,723,248 A | 11/1955 | Wright | |
| 3,161,460 A | 12/1964 | Huber | |
| 3,504,862 A | 4/1970 | Lowry | |
| 3,579,629 A | 5/1971 | Pasero et al. | |
| 3,589,978 A | 6/1971 | Kamal et al. | |
| 3,628,733 A * | 12/1971 | Kahn | B05B 1/14 239/337 |
| 3,716,633 A | 2/1973 | Viout et al. | |
| 3,767,125 A * | 10/1973 | Gehres | B65D 83/20 239/552 |
| 3,792,068 A | 2/1974 | Luedders et al. | |
| 3,810,977 A | 5/1974 | Levine et al. | |
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,128,631 A | 12/1978 | Landmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,389,752 A | 6/1983 | Briner et al. | |
| 4,401,271 A * | 8/1983 | Hansen | B65D 83/303 239/337 |
| 4,450,151 A | 5/1984 | Shinozawa | |
| 4,557,916 A | 12/1985 | Withiam | |
| 4,605,553 A | 8/1986 | Passalacqua | |
| 4,693,925 A | 9/1987 | Cheung et al. | |
| 4,728,571 A | 3/1988 | Clemens et al. | |
| 4,822,596 A | 4/1989 | Callingham et al. | |
| 4,871,529 A | 10/1989 | Sramek | |
| 4,874,554 A | 10/1989 | Lange et al. | |
| 4,957,732 A | 9/1990 | Grollier et al. | |
| 4,972,037 A | 11/1990 | Garbe et al. | |
| 4,983,377 A | 1/1991 | Murphy et al. | |
| 5,297,739 A | 3/1994 | Allen | |
| 5,300,284 A | 4/1994 | Wiechers et al. | |
| 5,508,259 A | 4/1996 | Holzner et al. | |
| 5,538,717 A | 7/1996 | La Poterie | |
| 5,614,173 A | 3/1997 | Ulmer et al. | |
| 5,643,557 A | 7/1997 | Eteve et al. | |
| 5,690,924 A | 11/1997 | Keil et al. | |
| 5,879,669 A | 3/1999 | Clausen et al. | |
| 5,900,241 A | 5/1999 | Roulier et al. | |
| 6,106,813 A | 8/2000 | Mondet et al. | |
| 6,166,093 A | 12/2000 | Mougin et al. | |
| 6,210,689 B1 | 4/2001 | Martino et al. | |
| 6,245,324 B1 | 6/2001 | Hough et al. | |
| 6,319,959 B1 | 11/2001 | Mougin et al. | |
| 6,350,434 B1 | 2/2002 | Bhatt et al. | |
| 6,372,876 B1 | 4/2002 | Kim et al. | |
| 6,395,265 B1 | 5/2002 | Mougin et al. | |
| 6,415,992 B1 | 7/2002 | Blondeel et al. | |
| 6,589,509 B2 | 7/2003 | Keller et al. | |
| 6,592,854 B1 | 7/2003 | Dupuis | |
| 6,751,886 B2 | 6/2004 | Chang et al. | |
| 7,063,834 B2 | 6/2006 | Mougin et al. | |
| 7,585,824 B2 | 9/2009 | Popplewell et al. | |
| 10,532,880 B2 | 1/2020 | Smail et al. | |
| 2002/0017575 A1 | 2/2002 | Andrews et al. | |
| 2002/0031478 A1 | 3/2002 | Keller et al. | |
| 2002/0150546 A1 | 10/2002 | Mougin et al. | |
| 2003/0150624 A1 | 8/2003 | Rummel | |
| 2003/0150937 A1 | 8/2003 | Laidler et al. | |
| 2003/0163878 A1 | 9/2003 | Pruche | |
| 2003/0185777 A1 | 10/2003 | Banowski et al. | |
| 2003/0191271 A1 | 10/2003 | Mondet et al. | |
| 2004/0047812 A1 | 3/2004 | Pataut et al. | |
| 2004/0170575 A1 | 9/2004 | Belli et al. | |
| 2004/0175404 A1 | 9/2004 | Shefer et al. | |
| 2005/0163737 A1 | 7/2005 | Lemoine et al. | |
| 2005/0220723 A1 | 10/2005 | Benabdillah et al. | |
| 2005/0224524 A1 * | 10/2005 | Khan | C07D 413/06 222/402.13 |
| 2008/0019928 A1 | 1/2008 | Franzke et al. | |
| 2008/0172807 A1 | 7/2008 | Brun | |
| 2008/0274071 A1 | 11/2008 | Kaplan et al. | |
| 2009/0061004 A1 | 3/2009 | Birkel et al. | |
| 2009/0218418 A1 | 9/2009 | Sharief | |
| 2010/0040572 A1 | 2/2010 | Mougin | |
| 2012/0097180 A1 | 4/2012 | Harris et al. | |
| 2012/0171264 A1 * | 7/2012 | Bernet | A61K 8/0225 424/401 |
| 2012/0258052 A1 * | 10/2012 | Mueller | A61Q 5/06 424/47 |
| 2012/0282190 A1 * | 11/2012 | Hammer | A61K 8/046 424/47 |
| 2013/0289080 A1 | 10/2013 | Masse et al. | |
| 2013/0340786 A1 | 12/2013 | Rodrigues et al. | |
| 2014/0030196 A1 | 1/2014 | Russell et al. | |
| 2014/0079747 A1 | 3/2014 | Dihora et al. | |
| 2015/0041559 A1 | 2/2015 | Albisetti | |
| 2015/0104397 A1 | 4/2015 | Smail et al. | |
| 2015/0122833 A1 * | 5/2015 | Baudin | B65D 83/34 222/402.1 |
| 2015/0139917 A1 | 5/2015 | Gawtrey et al. | |
| 2016/0075501 A1 | 3/2016 | Aubert et al. | |
| 2016/0100667 A1 | 4/2016 | Aubert et al. | |
| 2016/0106634 A1 | 4/2016 | Gawtrey et al. | |
| 2018/0000700 A1 | 1/2018 | Smail et al. | |
| 2018/0016087 A1 | 1/2018 | Smail et al. | |
| 2018/0243763 A1 | 8/2018 | Eurippini | |

FOREIGN PATENT DOCUMENTS

| | | |
|---|---|---|
| DE | 102008035013 A1 | 1/2010 |
| EP | 0080976 A1 | 6/1983 |
| EP | 0095238 A2 | 11/1983 |
| EP | 0186507 A2 | 7/1986 |

(56) References Cited

FOREIGN PATENT DOCUMENTS

| | | |
|---|---|---|
| EP | 0342834 A2 | 11/1989 |
| EP | 0412704 A2 | 2/1991 |
| EP | 0412707 A1 | 2/1991 |
| EP | 0452208 A1 | 10/1991 |
| EP | 0530974 A1 | 3/1993 |
| EP | 0582152 A2 | 2/1994 |
| EP | 0619111 A1 | 10/1994 |
| EP | 0637600 A1 | 2/1995 |
| EP | 0648485 A1 | 4/1995 |
| EP | 0751162 A1 | 1/1997 |
| EP | 0 974 332 A1 | 1/2000 |
| EP | 1026220 A1 | 8/2000 |
| EP | 1407754 A1 | 4/2004 |
| EP | 2444160 A1 | 4/2012 |
| EP | 2777770 A1 | 9/2014 |
| FR | 1222944 A | 6/1960 |
| FR | 1400366 A | 5/1965 |
| FR | 1564110 A | 3/1968 |
| FR | 1578989 * | 5/1968 ............... A61K 8/04 |
| FR | 1580545 A | 9/1969 |
| FR | 1600138 A | 7/1970 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004901 A1 | 10/2014 |
| FR | 3004902 A1 | 10/2014 |
| FR | 3004929 A1 | 10/2014 |
| FR | 3031437 A1 | 7/2016 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| GB | 2340891 A | 3/2000 |
| JP | 2003-326197 A | 11/2003 |
| JP | 2004-161339 A | 6/2004 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/045573 A1 | 6/2003 |
| WO | 03/049711 A2 | 6/2003 |
| WO | WO-2004043608 A1 * | 5/2004 ............... B05B 1/14 |
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177649 A1 | 11/2014 |
| WO | 2016/001190 A1 | 1/2016 |
| WO | 2016005703 A1 | 1/2016 |
| WO | 2016066729 A1 | 5/2016 |
| WO | 2016066730 A1 | 5/2016 |
| WO | 2016/092109 A1 | 6/2016 |
| WO | 2016/110575 A1 | 7/2016 |
| WO | 2016/110578 A1 | 7/2016 |
| WO | 2016/110579 A1 | 7/2016 |
| WO | 2018/162701 A1 | 9/2018 |
| WO | 2018/162707 A1 | 9/2018 |
| WO | 2018/162711 A1 | 9/2018 |

OTHER PUBLICATIONS

WO 2004043608 English Translation. AKAO. (Year: 2004).*
FR 1578989 English Translation. Modrach. (Year: 1968).*
Final Office Action for co-pending U.S. Appl. No. 14/399,753, dated Sep. 30, 2016.
Non-Final Office Action for co-pending U.S. Appl. No. 14/888,002, dated Sep. 9, 2016.
Non-Final Office Action for co-pending U.S. Appl. No. 14/787,983, dated Sep. 15, 2016.
International Search Report for PCT/EP2014/058896, dated Sep. 23, 2014.
International Search Report and Written Opinion for PCT/EP2014/058892, dated Oct. 29, 2014.
International Search Report for PCT/EP2014/058894, dated Sep. 29, 2014.
English language abstract for EP 0080976 A1 (Jun. 8, 1983).
English language abstract for FR 2357241 A2 (Feb. 3, 1978).
English language abstract for FR 2980125 A1 (Mar. 22, 2013).
English language abstract for JP 2004-161339 A (Jun. 10, 2004).
English language abstract for WO 02/078653 A1 (Oct. 10, 2002).
Brunauer, Stephen et al., "Adsorption of Gases in Multimolecular Layers," Journal of the American Chemical Society, vol. 60, Feb. 1938, p. 309-319.
International Search Report for counterpart Application No. PCT/EP2013/0509382, dated Jun. 20, 2014.
International Search Report for counterpart Application No. PCT/EP2013/059393, dated Jun. 20, 2014.
Database WPI Week 201172, Thomas Scientific, London, GB, AN 2011-N36295, XP002690571 (Jan. 25, 2013).
Mintel: Apr. 2010, "Refresh Dry Shampoo".
Mintel: Jun. 2011, "Brown Hair Powder Shampoo".
Non-Final Office Action for co-pending U.S. Appl. No. 14/399,753, dated Sep. 8, 2015.
Final Office Action for co-pending U.S. Appl. No. 14/399,753, dated Mar. 30, 2016.
Non-Final Office Action for co-pending U.S. Appl. No. 14/399,764, dated Dec. 17, 2015.
Final Office Action for co-pending U.S. Appl. No. 14/399,764, dated Aug. 5, 2016.
Non-Final Office Action for copending U.S. Appl. No. 14/399,764, dated Mar. 8, 2017.
Final Office Action for copending U.S. Appl. No. 14/787,983, dated May 30, 2017.
International Search Report for counterpart Application No. PCT/FR2015/051896, dated Oct. 19, 2015.
International Search Report for counterpart Application No. PCT/EP2015/075061, dated Jan. 20, 2016.
International Search Report for counterpart Application No. PCT/EP2015/075062, dated Jan. 26, 2016.
Mintel: "Code 10 Hair Styling Cream," XP007923186 (Sep. 2001).
Mintel: "One More Day Dry Shampoo," XP007923187 (Aug. 2013).
Mintel: "Foot Deodorant Spray," XP007923193 (Jan. 2014).
Mintel: "72h Anti-Perspirant Deodorant," XP007923192 (Jan. 2014).
Mintel: "Dry Shampoo," XP007923191 (Jan. 2014).
Non-Final Office Action for copending U.S. Appl. No. 15/324,804, dated Mar. 5, 2018.
Non-Final Office Action for copending U.S. Appl. No. 15/523,232, dated Feb. 23, 2018.

(56) References Cited

OTHER PUBLICATIONS

Bezard et al., "Triglycerides of Coconut Oil," Journal of American Oil Society, 48, 3, Mar. 1971, pp. 134-139.
Non-Final Office Action for copending U.S. Appl. No. 15/523,242, dated Aug. 31, 2017.
Final Office Action for copending U.S. Appl. No. 14/888,002, dated Sep. 21, 2017.
Final Office Action for copending U.S. Appl. No. 14/399,764, dated Aug. 16, 2017.
Non-Final Office Action for copending U.S. Appl. No. 14/399,753, dated Oct. 4, 2017.
Final Office Action for copending U.S. Appl. No. 15/324,804, dated Nov. 30, 2018.
Non-Final Office Action for copending U.S. Appl. No. 14/399,764, dated Dec. 5, 2018.
International Search Report for counterpart Application PCT/EP2011/072617, dated Jul. 5, 2012.
Todd, Charles, et al., "Volatile Silicone Fluids for Cosmetic Formulations," Cosmetics and Toiletries, vol. 91, Jan. 1976, pp. 29-32.
International Search Report for counterpart Application PCT/EP2016/050295, dated Mar. 23, 2016.
International Search Report for counterpart Application PCT/EP2016/050299, dated Mar. 23, 2016.
International Search Report for counterpart Application PCT/EP2016/050300, dated Mar. 16, 2016.
Non-Final Office Action for copending U.S. Appl. No. 15/541,738, dated May 17, 2018.
Non-Final Office Action for copending U.S. Appl. No. 13/993,413, dated May 19, 2015.
Final Office Action for copending U.S. Appl. No. 13/993,413, dated Dec. 30, 2015.
Non-Final Office Action for copending U.S. Appl. No. 13/993,413, dated Nov. 8, 2017.
Final Office Action for copending U.S. Appl. No. 13/993,413, dated Jul. 5, 2018.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Final Office Action for copending U.S. Appl. No. 13/993,413, dated Nov. 14, 2016.
Non-Final Office Action for copending U.S. Appl. No. 14/787,983, dated May 11, 2018.
Non-Final Office Action for copending U.S. Appl. No. 15/523,242, dated Mar. 27, 2018.
Notice of Allowance for co-pending U.S. Appl. No. 15/541,738, dated Sep. 4, 2019.
Supplemental Notice of Allowance for co-pending U.S. Appl. No. 15/523,242, dated Sep. 5, 2019.
Non-Final Office Action for co-pending U.S. Appl. No. 15/322,771, dated Sep. 6, 2019.
Non-Final Office Action for co-pending U.S. Appl. No. 14/787,983, dated Jun. 26, 2019.
Final Office Action for co-pending U.S. Appl. No. 15/541,741, dated Jul. 11, 2019.
Final Office Action for copending U.S. Appl. No. 14/787,983, dated Dec. 27, 2018.
Final Office Action for copending U.S. Appl. No. 15/523,232, dated Jan. 25, 2019.
Non-Final Office Action for copending U.S. Appl. No. 15/541,738, dated Feb. 5, 2019.
Non-Final Office Action for copending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
Mintel: "Styling Mousse," XP002736036, Nov. 2008.
Mintel: "Clean Freak Refreshing Dry Shampoo," XP007923188, Demert Brands, Mar. 2014.
Final Office Action for co-pending U.S. Appl. No. 14/399,764, dated Jun. 7, 2019.
Notice of Allowance for co-pending U.S. Appl. No. 15/523,242, dated Jun. 12, 2019.
Non-Final Office Action for co-pending U.S. Appl. No. 15/324,804, dated Oct. 10, 2019.
Non-Final Office Action for co-pending U.S. Appl. No. 14/888,002, dated Oct. 7, 2019.
Non-Final Office Action for co-pending U.S. Appl. No. 15/541,743, dated Nov. 21, 2019.
Final Office Action for copending U.S. Appl. No. 15/322,771, dated Jul. 10, 2020.
Non-Final Office Action for copending U.S. Appl. No. 14/787,983, dated Jul. 15, 2020.
Non-Final Office Action for co-pending U.S. Appl. No. 15/541,741, dated Mar. 3, 2020.
CLEARCO, "Cyclo-1400-DM D5 Cyclomethicone/dimethicone blend," ([retrieved from on-line website: http://www.clearcoproducts.com/cyclo-1400-d5-blend.hlml], 2013, pp. 1-2.
Wayback Machine to support publication year of CLEARCO (Year: 2013).
Non-Final Office Action for co-pending U.S. Appl. No. 15/523,232, dated Feb. 20, 2020.
Final Office Action for co-pending U.S. Appl. No. 14/787,983, dated Feb. 26, 2020.
Final Office Action for copending U.S. Appl. No. 15/541,741, dated Sep. 17, 2020.
Final Office Action for copending U.S. Appl. No. 15/523,232, dated Oct. 1, 2020.
Final Office Action for copending U.S. Appl. No. 15/324,804, dated Apr. 20, 2020.
Notice of Allowance for copending U.S. Appl. No. 15/541,743, dated Mar. 18, 2020.
Non-Final Office Action for copending U.S. Appl. No. 15/322,771, dated Mar. 20, 2020.
Final Office Action for copending U.S. Appl. No. 14/888,002, dated Jun. 1, 2020.
Final Office Action for copending U.S. Appl. No. 14/787,983, dated Feb. 19, 2021.
Non-Final Office Action for copending U.S. Appl. No. 15/322,771, dated Mar. 2, 2021.
International Search Report and Written Opinion for counterpart Application No. PCT/EP2018/055882, dated May 4, 2018.
International Search Report and Written Opinion for counterpart Application No. PCT/EP2018/055889, dated May 4, 2018.
International Search Report and Written Opinion for counterpart Application No. PCT/EP2018/055904, dated Apr. 30, 2018.
Final Office Action for copending U.S. Appl. No. 16/491,375, dated May 26, 2020.
Non-Final Office Action for copending U.S. Appl. No. 16/491,375, dated Nov. 25, 2019.
Non-Final Office Action for copending U.S. Appl. No. 16/491,372, dated May 28, 2020.
NPL search string: IQQueryQuickExport 202005221756, downloaded May 22, 2020.
MPL search string IQQueryQuickExport 202005221759, downloaded May 22, 2020.
Final Office Action for copending U.S. Appl. No. 16/491,372, dated Dec. 18, 2020.
Non-Final Office Action for copending U.S. Appl. No. 16/491,374, dated Jan. 14, 2021.
Non-Final Office Action for copending U.S. Appl. No. 15/541,741, dated May 27, 2021.
Final Office Action for copending U.S. Appl. No. 16/491,374, dated Jun. 28, 2021.
Non-Final Office Action for copending U.S. Appl. No. 14/888,002, dated Sep. 3, 2021.
Non-Final Office Action for copending U.S. Appl. No. 16/491,372, dated Jul. 12, 2021.
Non-Final Office Action for copending U.S. Appl. No. 16/491,374, dated Oct. 20, 2021.

(56) References Cited

OTHER PUBLICATIONS

Non-Final Office Action for copending U.S. Appl. No. 14/888,002, dated Sep. 23, 2022.

* cited by examiner

MULTI-DIFFUSION-ORIFICE AEROSOL DEVICE FOR DRY-WASHING THE HAIR

CROSS REFERENCE TO RELATED APPLICATION

This is a national stage application of PCT/EP2014/058894, filed internationally on Apr. 30, 2014, which claims priority to French Application No. 1354012, filed on Apr. 30, 2013, all of which are incorporated herein by their entireties.

The present invention relates to a particular aerosol device comprising a cosmetic composition based on at least one sebum-absorbing powder, and to the use thereof for the dry-washing and cosmetic treatment of keratin materials, preferably human keratin fibres such as the hair.

In the field of washing keratin materials, dry shampoos have existed for many years, either in a powder form or in aerosol form. They enable excess sebum to be removed quickly and without wetting the head of hair. They act by taking up sebum by absorption by means of powders chosen for their sebum-absorbing qualities.

The powders used may be of mineral, organic or synthetic origin and may be wheat, rice and corn starch derivatives.

In practice, the proposed dry shampoos are not entirely satisfactory, especially in terms of application and comfort. The aerosol sprays conventionally used generate a conical spray. This type of spray is not optimal for a localized application, especially at the root, and is generally uncomfortable on application due to the relatively large impact force on the head of hair.

There is thus a need to develop a novel aerosol device comprising a dry shampoo composition that is comfortable on application.

There is also a need to develop such a device which affords optimum cleansing activity and gives the head of hair volume.

The Applicant has found, surprisingly and advantageously, that the use of a means for dispensing the said aerosol composition comprising a diffuser equipped with at least two spray orifices for dispensing at least one sebum-absorbing powder can facilitate the application of the composition with better dispersion and afford greater comfort on application, while at the same time offering the cleansing properties expected of a dry shampoo. Document US2012/0282190 describes for example a dry shampoo sprayed with a classical diffuser.

Moreover, the composition leaves a smaller amount of white residue than the products conventionally used.

One subject of the invention is thus an aerosol device comprising:
- a container containing:
  - one or more propellants, and
  - a composition comprising one or more sebum-absorbing powders with a sebum uptake of greater than or equal to 35 ml/100 g,
  - the propellant(s) possibly being present in the composition or, in the container, separate from the composition,
- a means for dispensing the said aerosol composition, comprising a diffuser equipped with at least two, and better three, spray orifices.

This particular combination affords comfort on application by limiting the impact force of the spray on the head of hair.

It also makes it possible to facilitate the application and distribution of the hair composition homogeneously at the root of the head of hair, and thus affords optimum cleansing.

Moreover, the composition leaves a smaller amount of white residue while at the same time being more styling than the known products.

By combining the sebum-absorbing powder with a styling powder comprising one or more water-insoluble mineral compounds, it is also possible to obtain a styling effect, especially for giving the head of hair volume and body and for lifting the roots.

The present invention also relates to a process for the dry-washing and cosmetic treatment of keratin materials, especially human keratin fibres such as the hair, comprising the spraying using an aerosol device according to the invention, onto the keratin materials, of the composition according to the invention.

A subject of the invention is also the use of the cosmetic composition sprayed from this aerosol device for the dry-washing and cosmetic treatment of keratin materials, preferably human keratin materials and better still the hair.

Other subjects, characteristics, aspects and advantages of the invention will emerge even more clearly on reading the description and the example that follows.

In the text hereinbelow, unless otherwise indicated, the limits of a range of values are included in that range, especially in the expressions "between" and "ranging from . . . to . . . ".

Moreover, the expression "at least one" used in the present description is equivalent to the expression "one or more".

According to the invention, the aerosol device comprises a container which contains a cosmetic composition comprising one or more sebum-absorbing powders with a sebum uptake of greater than or equal to 35 ml/100 g.

For the purposes of the present invention, the term "sebum-absorbing powder" means a powder that is capable of absorbing and/or adsorbing sebum, which has a sebum uptake of greater than or equal to 35 ml/100 g.

The sebum uptake corresponds to the amount of sebum absorbed and/or adsorbed by the powder. It is expressed in ml of sebum per 100 g of powder and is measured using the method for determining the oil uptake of a powder described in standard NF T 30-022.

The oil uptake of a powder corresponds to the amount of sebum absorbed onto the available surface of the powder by measuring the "wet point" as indicated below.

The measuring method is as follows: an amount m (in grams) of between 0.5 and 5 g of powder is placed on a glass plate, the amount depending on the density of the powder, followed by dropwise addition of artificial sebum having the following composition:

| | |
|---|---|
| triolein | 29% by weight |
| oleic acid | 28.5% by weight |
| oleyl oleate | 18.5% by weight |
| squalene | 14% by weight |
| cholesterol | 7% by weight |
| cholesteryl palmitate | 3% by weight |

After addition of 4 to 5 drops of artificial sebum, the artificial sebum is incorporated into the powder using a spatula, and addition of the artificial sebum is continued until conglomerates of artificial sebum and powder have formed. From this point, the artificial sebum is added at a rate of one drop at a time and the mixture is subsequently triturated with the spatula.

The addition of artificial sebum is stopped when a firm, smooth paste is obtained. This paste must be able to be spread on the glass plate without cracking or forming lumps. The volume Vs, in ml, of artificial sebum used is then noted.

The sebum uptake corresponds to the ratio Vs/m.

The sebum-absorbing powder(s) used in the aerosol device of the invention have a preferable sebum uptake ranging from 35 to 1000 ml/100 g and better still from 35 to 800 ml/100 g.

Advantageously, the sebum-absorbing particle may have a BET specific surface area of greater than or equal to 150 $m^2/g$, preferably greater than or equal to 300 $m^2/g$, better still greater than 500 $m^2/g$ and preferentially greater than 600 $m^2/g$, and especially less than 1500 $m^2/g$.

The BET specific surface area is determined according to the BET (Brunauer-Emmett-Teller) method described in the Journal of the American Chemical Society, vol. 60, page 309, February 1938, which corresponds to International Standard ISO 5794/1 (appendix D). The BET specific surface area corresponds to the total specific surface area (thus including micropores) of the particle and especially of the powder.

The sebum-absorbing powder may be a mineral powder or an organic powder.

More specifically, the sebum-absorbing powder may be chosen from:
  starches,
  calcium silicates,
  perlites,
  zeolites,
  polylactic acids,
  silicas,
  polyamide (Nylon®) powders,
  powders of acrylic polymers, especially of polymethyl methacrylate, of poly(methyl methacrylate/ethylene glycol dimethacrylate), of poly(allyl methacrylate/ethylene glycol dimethacrylate), or of ethylene glycol dimethacrylate/lauryl methacrylate copolymer;
  silicone elastomer powders, obtained especially by polymerization of organopolysiloxane containing at least two hydrogen atoms each bonded to a silicon atom and of an organopolysiloxane comprising at least two ethylenically unsaturated groups (especially two vinyl groups) in the presence of a platinum catalyst; and mixtures thereof.

The sebum-absorbing powder may be a powder coated with a hydrophobic treatment agent.

The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate (ITT), and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The term "alkyl" mentioned in the compounds cited above denotes in particular an alkyl group containing from 1 to 30 carbon atoms and preferably containing from 5 to 16 carbon atoms.

The starches that may be used in the present invention are, for example, corn starch, potato starch, tapioca starch, rice starch, wheat starch and cassava starch.

The starches may be modified or unmodified.

A modified starch is a starch that is been modified via processes known to those skilled in the art, for instance esterification, etherification, oxidation, acidic hydrolysis, crosslinking or enzymatic conversion.

Non-limiting examples of modified starches include aluminium starch octenylsuccinate, sodium starch octenylsuccinate, calcium starch octenylsuccinate, distarch phosphate, hydroxyethyl starch phosphate, hydroxypropyl starch phosphate, sodium carboxymethyl starch and sodium starch glycolate.

In a particular embodiment, the starch is a starch octenylsuccinate, in particular of aluminium, the starch being corn, wheat or rice starch. Mention may be made especially of the product sold by Akzo Nobel under the name Dry Flo Plus.

Preferably, the calcium silicates used as sebum-absorbing powder have a sebum uptake of greater than 200 ml/100 g, better still between 400 ml/100 g and 600 ml/100 g and more preferentially of about 475 ml/100 g.

The specific surface area (BET) preferably ranges from about 150 $m^2/g$ to 600 $m^2/g$, better still from 300 $m^2/g$ to 600 $m^2/g$ and even more preferentially from 310 $m^2/g$ to 350 $m^2/g$.

The size of the silicate particles is preferably less than 20 micrometres.

These calcium silicates are generally prepared by reaction of reactive silica with an alkaline-earth metal reagent, preferably an alkaline-earth metal oxide or hydroxide, and a source of aluminium such as sodium aluminate or alumina. Since the final properties of the silicate depend on the reactivity of the silica, the preferred source of silica is the product of reaction of a soluble silicate, such as sodium silicate, and of a mineral acid such as sulfuric acid. Suitable amorphous synthetic alkaline-earth metal silicates are manufactured by the company JM Huber Corporation and are sold under the name Hubersorb®. Methods for preparing these silicas are disclosed in greater detail in U.S. Pat. No. 4,557,916. Other suitable silicates are available from JM Huber Corporation, for instance the sodium aluminosilicate sold under the brand name Zeolexg and the sodium magnesium aluminosilicate sold under the brand name Hydrex®.

Sebum-absorbing powders that may also be used include perlites, which are generally aluminosilicates of volcanic origin and whose composition is as follows:
  70.0-75.0% by weight of silica $SiO_2$
  12.0-15.0% by weight of oxide of aluminium oxide $Al_2O_3$
  3.0-5.0% of sodium oxide $Na_2O$
  3.0-5.0% of potassium oxide $K_2O$
  0.5-2% of iron oxide $Fe_2O_3$
  0.2-0.7% of magnesium oxide MgO
  0.5-1.5% of calcium oxide CaO
  0.05-0.15% of titanium oxide $TiO_2$ Examples of zeolites that may especially be mentioned include sodium or potassium aluminosilicate compounds such as the product sold by Zeochem under the name Xmol.

The polylactic acids that may be used in the present invention are especially Accurel EP600 from Akzo Nobel or the product sold under the name Lactic Acid Polymer 9105 by Dajac Labs.

Silica powders that may be mentioned include:
  the porous silica microspheres sold under the name Silica Beads SB-700 by the company Miyoshi; Sunsphere® H51, Sunsphere® H33 by the company Asahi Glass;
  the polydimethylsiloxane-coated amorphous silica microspheres sold under the name SA Sunsphere® H33 and SA Sunsphere® H53 by the company Asahi Glass.

A Nylon powder that may be mentioned is the Nylon powder sold under the name Orgasol® 4000 by the company Atochem.

Acrylic polymer powders that may be mentioned include:
the polymethyl methacrylate powders sold under the name Covabead® LH85 by the company Wackherr;
the polymethyl methacrylate/ethylene glycol dimethacrylate powders sold under the name Dow Corning 5640 Microsponge® Skin Oil Adsorber by the company Dow Corning; Ganzpearl® GMP-0820 by the company Ganz Chemical;
the polyallyl methacrylate/ethylene glycol dimethacrylate powders sold under the name Poly-Pore® L200 or Poly-Pore® E200 by the company Amcol Health and Beauty Solutions Inc.; these powders especially have a sebum uptake of greater than or equal to 1 ml/g, better still ranging from 1 ml/g to 20 ml/g;
the ethylene glycol dimethacrylate/lauryl methacrylate copolymer powders sold under the name Polytrap® 6603 from the company Dow Corning.

Silicone elastomer powders that may be mentioned include the powders sold under the names Trefil® Powder E-505C and Trefil® Powder E-506C by the company Dow Corning.

Preferably, the sebum-absorbing powder is chosen from modified starches such as starch octenylsuccinates, in particular of aluminium, perlite, polylactic acids and zeolites, and better still from starch octenylsuccinates.

When propellant(s) are present in the composition, the sebum-absorbing powder(s) are present in an amount preferably ranging from 0.1% to 90% by weight, better still from 1% to 30% by weight and even more preferentially from 2% to 15% by weight relative to the total weight of the composition.

The composition may also comprise one or more styling powders comprising one or more water-insoluble mineral compounds other than the sebum-absorbing powders.

The term "styling powder" means a powder consisting of one or more water-insoluble mineral compounds having a capacity for shaping the head of hair or for the durability of this shaping.

The water-insoluble mineral compound(s) are chosen from metal carbonates, oxides and sulfates, and silicates containing magnesium.

For the purposes of the present invention, the term "water-insoluble" refers to a compound whose solubility at spontaneous pH in water at 25° C. and at atmospheric pressure is less than 0.1%.

Examples that may be mentioned more particularly include carbonates, oxides and sulfates of alkaline-earth metals such as beryllium, magnesium, calcium, strontium, barium and radium, better still magnesium and calcium; oxides, sulfates and carbonates of aluminium, of gallium and of indium; and silicates containing magnesium, in particular those containing an amount of magnesium of greater than 10% by weight (on a dry basis) expressed as magnesium oxide, such as Li—Mg—Na silicates, for instance Laponite XLG sold by the company Rockwood.

More preferably, use will be made of calcium carbonate, magnesium carbonate, alumina, barium sulfate and/or magnesium oxide, and better still calcium carbonate. Preferably, these compounds have a mean particle size of from 20 to 50 μm, as water-insoluble mineral compound(s).

When they are present, the water-insoluble mineral compound(s) are present in an amount ranging from 0.1% to 30% by weight, better still from 0.5% to 15% by weight and even more preferentially from 1% to 10% by weight relative to the total weight of the composition, when the propellant(s) are present in the composition.

The composition may also comprise one or more $C_{2-4}$ monoalcohols.

As $O_{2-4}$ monoalcohol(s) that may be used in the aerosol device of the invention, mention may be made especially of ethanol or isopropanol, and better still ethanol.

When they are present, the $C_{2-4}$ monoalcohol(s) are preferably present in an amount ranging from 1% to 70% by weight, better still from 5% to 60% by weight and even more preferentially from 10% to 50% by weight relative to the total weight of the composition, when the propellant(s) are present in the composition.

The composition according to the invention may contain one or more additional organic solvents such as polyols, for instance glycerol, propylene glycol or polyethylene glycols.

It may also contain water.

Preferably, the composition according to the invention contains less than 5% by weight of water relative to the total weight of the composition, when the propellant(s) are present in the composition. Even more preferentially, it does not contain any added water. The composition is then said to be anhydrous.

The container of the device according to the invention also comprises one or more propellants.

Examples of propellants that may be used in the aerosol device of the present invention are liquefied gases such as dimethyl ether, 1,1-difluoroethane, or $C_{3-5}$ alkanes, for instance propane, isopropane, n-butane, isobutane or pentane, or compressed gases such as air, nitrogen or carbon dioxide, and mixtures thereof.

Mention may be made preferentially of $C_{3-5}$ alkanes and in particular propane, n-butane and isobutane, and mixtures thereof.

The agent(s) may be present in the composition or, as a variant, in the container containing the composition, but separate from the composition.

The agent(s) are preferably present in the composition.

When the propellant(s) are present in the composition, they are preferably present in an amount ranging from 10% to 90% by weight, better still from 15% to 80% by weight and even more preferentially from 20% to 75% by weight relative to the total weight of the composition.

Preferably, the composition of the invention may also comprise one or more silicones other than silicone elastomers.

Preferably, the additional silicone(s) are silicone gums.

The silicone gums that may be present in the composition according to the invention are especially polydiorganosiloxanes, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Examples of silicone gums that may be mentioned more particularly include the following products:
polydimethylsiloxane gums,
polydimethylsiloxane-α,ω-disilanol gums,
polydimethylsiloxane/methylvinylsiloxane gums,
polydimethylsiloxane/diphenylsiloxane gums,
polydimethylsiloxane/phenylmethylsiloxane gums,
polydimethylsiloxane/diphenylsiloxane/methylvinylsiloxane gums.

Products that may be used more particularly are the following mixtures:
mixtures formed from a polydimethylsiloxane hydroxylated at the end of the chain (known as dimethiconol according to the nomenclature of the CTFA dictionary) and from a linear polydimethylsiloxane (known as dimethicone according to the nomenclature of the CTFA dictionary), such as the product Mirasil D-DML sold by the company Dow Corning, mixtures formed from a polydimethylsiloxane hydroxylated at the end of the chain (known as dimethiconol according to the nomenclature of the CTFA dictionary) and from a cyclic polydimethylsiloxane (known as cyclomethicone according to the nomenclature of the CTFA dictionary), such as the product Q2 1401 sold by the company Dow Corning.

The high-viscosity silicone gums used in the invention generally have a viscosity of greater than or equal to $0.5 \times 10^{-3}$ m$^2$/s (500 cSt), preferably ranging from $1 \times 10^{-3}$ to $10 \times 10^{-3}$ m$^2$/s. The viscosity is measured using a Brookfield viscometer at 25° C.

When the non-elastomeric silicone(s) are present in the device of the invention, their amount preferably ranges from 0.05% to 5% by weight relative to the total weight of the composition, when the propellant(s) are present in the composition.

The composition of the invention also optionally comprises one or more fatty esters.

The fatty esters optionally used in the invention are liquid or non-liquid.

The term "liquid fatty ester" means an ester derived from a fatty acid and/or from a fatty alcohol that is liquid at standard temperature (25° C.) and at atmospheric pressure (760 mmHg, i.e. $1.013 \times 10^5$ Pa).

The esters are preferably liquid esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates, preferably of $C_2$-$C_{22}$, such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made especially of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, and polyesters, and mixtures thereof.

These esters may be, for example, oleates, laurates, palmitates, myristates, behenates, cocoates, stearates, linoleates, linolenates, caprates or arachidonates, or mixtures thereof, such as, especially, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates.

An example that may be mentioned is the product sold under the name Glucate® DO by the company Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, safflower oil, candlenut oil, camellina oil, tamanu oil, babassu oil and pracaxi oil, caprylic/capric acid triglycerides, for instance those sold by the company Stéarineries Dubois or those sold under the names Miglyol® 810, 812 and 818 by the company Dynamit Nobel, jojoba oil and shea butter oil.

Fatty esters that will preferably be used include liquid fatty esters derived from monoalcohols, such as isopropyl myristate or palmitate, and more particularly isopropyl myristate.

The non-liquid fatty esters are especially solid esters derived from $C_9$-$C_{26}$ fatty acids and from $C_9$-$C_{26}$ fatty alcohols.

Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Examples that may especially be mentioned include diethyl sebacate, diisopropyl sebacate, diisopropyl adipate, di-n-propyl adipate, dioctyl adipate and dioctyl maleate.

Among all the esters mentioned above, it is preferred to use myristyl, cetyl or stearyl palmitates, and alkyl myristates such as cetyl myristate, stearyl myristate and myristyl myristate.

When the fatty ester(s) are present in the device of the invention, their amount preferably ranges from 0.1% to 30% by weight and better still from 1% to 10% by weight relative to the total weight of the composition, when the propellant(s) are present in the composition.

The composition contained in the aerosol device of the invention may also comprise propylene carbonate, preferably in an amount ranging from 0.05% to 5% by weight relative to the total weight of the composition, when the propellant(s) are present in the composition.

The compositions defined in the invention may also contain one or more additives chosen from conditioning or fixing anionic, cationic, nonionic, amphoteric or zwitterionic polymers, fragrances, dyes, protective screening agents, acids, bases, nacres and glitter flakes.

These additives may be present in the composition according to the invention in an amount ranging from 0 to 20% by weight relative to the total weight of the composition, when the propellant(s) are present in the composition. A person skilled in the art will take care to select these optional additives and the amounts thereof such that they do not harm the properties of the compositions of the present invention.

The compositions in accordance with the invention are conditioned in an aerosol device comprising a container, also known as a reservoir.

The container is pressurized and comprises the composition to be dispensed. The container containing the pressurized composition may be opaque or transparent. It can be made of glass, of polymer or of metal, optionally covered with a protective lacquer layer.

As already mentioned previously, the container contains both the propellant(s) and the other ingredients of the composition, in a single compartment, or as a variant in two compartments. According to the latter variant, the container may consist of an outer aerosol can comprising an inner bag hermetically welded to a valve. The various ingredients of the composition are introduced into the inner bag and a propellant is introduced between the bag and the can at a sufficient pressure to make the product come out in the form of a spray.

The propellant may be a compressed gas that is preferably used at a pressure of between 1 and 12 bar and better still between 9 and 11 bar.

The container is equipped at its top end with a valve that seals the system. The valves that are suitable for the devices according to the invention are especially valves with an internal restriction orifice of between 0.3 and 3 mm, preferably between 1 and 2.5 mm and even more preferentially between 1.3 and 2 mm, and with a nozzle whose orifice is between 0.2 and 0.6 mm, preferably between 0.3 and 0.5 mm and even more preferentially between 0.35 and 0.45 mm in size.

They are in particular valves sold by the companies Precision, Coster, Seaquist and Lindal.

The device, conditioned with such a valve, ensures the sealing of the system, and also the dispensing of the product from the container.

The aerosol device according to the invention also comprises a means for dispensing the said aerosol composition comprising a diffuser equipped with at least two, or even three, spray orifices, provided to spray the composition in a main spraying direction Y.

In particular, the dispensing means on which the user can press to make the product come out fits to the valve.

This dispensing means comprises a diffuser.

The diffuser according to the invention is equipped with at least two spray orifices.

Preferably, the diffuser is equipped with three spray orifices.

The three spray orifices are advantageously arranged at 120° relative to each other around the spraying direction Y.

The orifices may have a single outlet, also known as a directional outlet, or turbulent channels.

The spray orifices may have axes that are parallel to each other and parallel to the spraying direction Y.

The spray orifices can terminate in a narrowing of their cross-section. For example, the spray orifices each comprise a cylindrical section which is connected to a corresponding feed channel, a conical section for reducing the cross-section and a final cylindrical section having a small diameter, from which the composition is ejected.

These orifices are present on one or more nozzles and preferably on only one nozzle.

Each orifice is fed via a feed channel, these channels emerging in a product delivery channel intended to be in communication with the valve.

The feed channels are preferably inclined obliquely relative to the spraying direction Y.

The term "oblique" should be understood as meaning neither parallel nor perpendicular.

The feed channels may extend along respective longitudinal axes which are preferably obliquely inclined relative to the axis Y by an angle of between 30° and 60°, and more preferably of the order of 45°. Preferably, the angle is the same for all the feed channels.

The invention may be understood more clearly on reading the following detailed description of a non-limiting implementation example thereof and on examining the appended drawings, in which.

Figure 1:
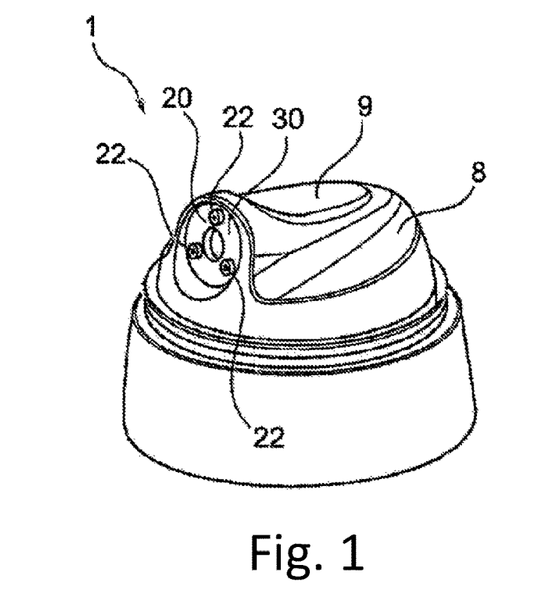
FIG. 1 represents in perspective, in isolation, a diffuser.
Figure 2:
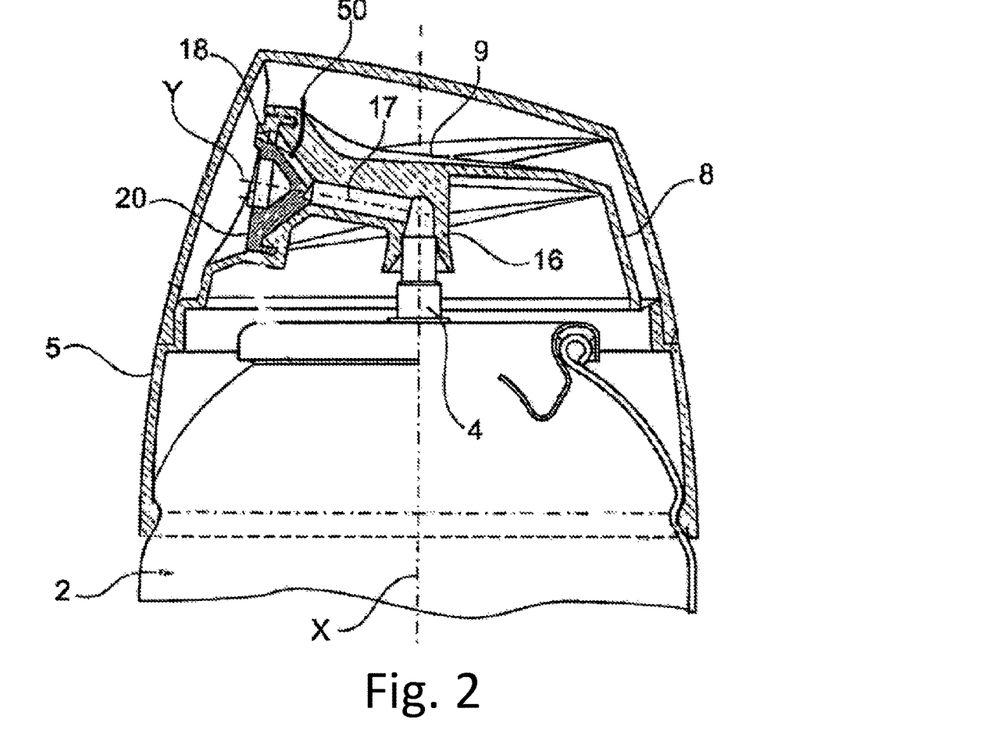
FIG. 2 represents the diffuser mounted on a container with a protective cap in place, in partial and diagrammatic longitudinal cross-section.
Figure 3:
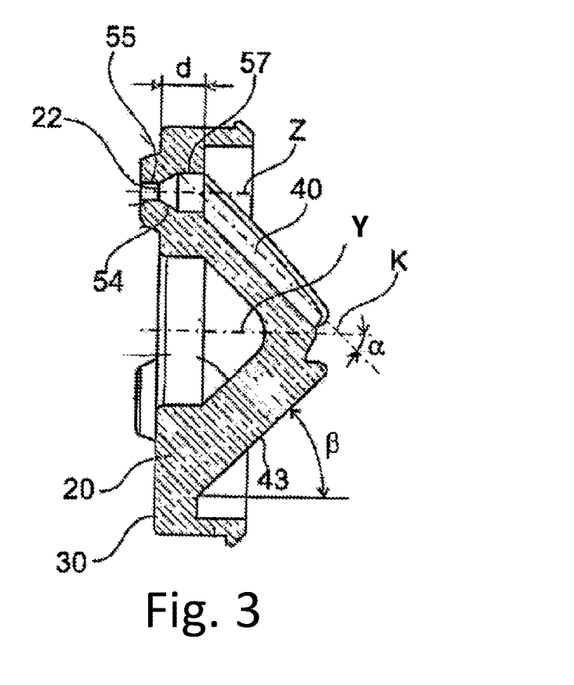
FIG. 3 represents, in isolation, in axial cross-section, the spray nozzle.

The diffuser 1 represented in the figures is intended to equip a container 2, for example an aerosol can comprising the composition described previously.

The container 2 is equipped with a valve triggered by pushing in a hollow control rod 4 along the longitudinal axis X of the container. As a variant, the valve is triggered by tipping.

In the example illustrated, the diffuser 1 comprises a body 5 which comprises a push button 8. The push button 8 defines a surface 9 on which the user can press to dispense the product.

The push button 8 is made with an end piece 16 interlocked over the valve rod 4, this end piece 16 being in communication with a delivery channel 17, the longitudinal axis Y of which is non-perpendicular to the longitudinal axis X of the container, being inclined upwards, when the container 2 is vertical and the dispensing head 1 is fixed above.

The delivery channel 17 emerges in the bottom of a housing 18, which receives a spray nozzle 20.

The nozzle 20 has several spray orifices 22, numbering three in the case in point, the axes Z of which are parallel to the spraying direction, which coincides with the longitudinal axis Y of the delivery channel 17 and with the axis of the nozzle.

The orifices 22 emerge on a front face 30 of the nozzle 20, which is visible after the nozzle has been fitted to the push button 8.

In the illustrated example, the nozzle 20 is without turbulent channels, the orifices 22 being directional.

The nozzle 20 comprises, on its rear face 43, which has a general dome shape, three recesses 40 each extending longitudinally along an axis K which forms, with the axis W of the nozzle 20, an angle α preferably of approximately 45°.

The recesses 40 define, with the bottom of the housing 18 of the push button 8 which receives them, feed channels 50 which connect the delivery channel 17 to the spray orifices 22.

Each feed channel 50 is connected to an axisymmetric section 57, having the axis Z. A conical section 54 converging towards the outlet connects the section 57 to another axisymmetric section 55, of smaller diameter, which emerges on the front face 30 of the nozzle.

The diameter of the cylindrical section 55 is, for example, 0.25 mm and that of the cylindrical section 57 is 0.6 mm. The axial dimension d of the conical section 54 and of the cylindrical section 57, considered together, is, for example, between 1 and 1.5 mm, for example being 1.3 mm, and the axial dimension of the cylindrical section 55 is, for example, between 0.4 and 0.8 mm, for example being 0.6 mm.

The outside diameter of the nozzle 20 is, for example, less than or equal to 15 mm. The spray orifices 22 may be relatively close together, which enables the formation at a short distance, for example less than 10 cm from the diffuser 1, of a homogeneous spray.

The present invention also relates to a process for the dry-washing and cosmetic treatment of the hair, comprising the application to the hair, preferably dry hair, of a cosmetic composition as described above by means of an aerosol device as described above.

The present invention also relates to the use of the cosmetic composition defined above sprayed from the aerosol device according to the invention, for the dry-washing and cosmetic treatment of the hair.

The examples that follow serve to illustrate the invention.

EXAMPLES

The following compositions 1 and 2 according to the invention were prepared from the compounds indicated in the table below, all the amounts being indicated as weight percentages of product as active materials relative to the total weight of the composition.

|  | 1 | 2 |
|---|---|---|
| Aluminium Starch Octenylsuccinate[1] | 8.6% | 9.39% |
| Calcium carbonate (D50 = 35 μm)[2] | 2% | 2.18% |
| Disteardimonium Hectorite[3] | 0.25% | 0.28% |
| Dimethicone/dimethiconol[4] | 0.55% | — |
| Isopropyl myristate | 2% | 0.42% |
| Propylene carbonate[5] | 0.07% | — |
| Fragrance | 0.2% | 0.20% |
| Isobutane | 70% | qs 100% |
| Ethanol | qs 100% | — |

[1]Sold under the trade name Dry Flo Plus by Akzo Nobel
[2]Sold under the trade name Omyacare S60 by Omya
[3]Sold under the trade name Bentone 38 VCG by Elementis
[4]Sold under the trade name Mirasil D-DML by Dow Corning
[5]Sold under the trade name JeffSol Propylene Carbonate by Huntsman The aerosol device according to the invention used for conditioning the above compositions comprises the following characteristics:

a valve equipped with a nozzle with an orifice 0.64 mm in size and an internal restriction orifice 0.64 mm in size, with an additional gas intake 0.64 mm in size, a diffuser, as illustrated on the figures, comprising three direct-outlet orifices 0.5 mm in diameter.

The compositions were sprayed onto a head of greasy, dirty hair. The diffusion is fine and the application is easy.

After drying, it is found that the head of hair is visually cleaner, with little visible residue. Lifting of the roots and provision of volume and body are also observed. The hair has a natural feel.

Composition A according to the invention was prepared from the compounds indicated in the table below, all the amounts being indicated in gram of commercial product as is.

|  | A |
|---|---|
| Disteardimonium Hectorite (Bentone 38 VCG sold by Elementis) | 3 |
| Aluminum starch octenylsuccinate (DRY FLO PLUS sold by Akzo Nobel) | 4 |
| Carbonate de calcium (D50 = 35 μm) (OMYACARE S60 sold by Omya) | 8 |
| Ethanol | 1.9 |
| Cyclomethicone (XIAMETER PMX-0245 CYCLOPENTASILOXANE sold by Dow Corning = | 4.90 |
| Silice | 0.2 |
| Isobutane | 78 |

Composition A was packaged in an aerosol device ($D_{ant}$) with a conventional diffuser with one orifice (prior art).

Composition A was also packaged in an aerosol device ($D_{inv}$) with a diffuser with three orifices, as described in the previous example (invention).

The evaluations were made by ten experts on natural hair locks attached on a rectangular support. Each support carries about 20 g of hair.

Hair were washed and allowed to dry naturally. 5.5 g of composition A were sprayed on the hair of a support, with the device ($D_{ant}$).

5.5 g of composition A were also sprayed on the hair of another support, with the device ($D_{inv}$).

The experts evaluated the whitening of the hair after the application of the composition.

They also evaluated the amount of residues on a comb comprising large and small teeth after having combed hair according to the following protocol: three passages of large teeth and three passages of small teeth.

They also evaluated the facility of the fingers to run through the hair after ten passages of fingers through the hair.

Ten out of ten experts felt that the hair treated with the composition A sprayed with aerosol device comprising a diffuser with three orifices of the invention ($D_{inv}$) are less white, that they lead to less residues on the comb, to an easier running of fingers through the hair, and a feel more smooth, homogeneous and without grip, compared to hair treated with the composition A sprayed with aerosol device comprising a diffuser with one orifice of the prior art ($D_{ant}$).

The invention claimed is:

1. An aerosol device comprising:
   (a) a container comprising:
      at least one propellant, and
      a composition comprising:
         from 8.6% to 30% by weight, based on the total weight of the composition and the at least one propellant, of at least one sebum-absorbing powder chosen from modified starches having a sebum uptake of greater than or equal to 35 ml/100 g; and from 1% to 10% by weight, based on the total weight of the composition and the at least one propellant, of a styling powder comprising at least one water-insoluble mineral compound chosen from calcium carbonate, magnesium carbonate, alumina, barium sulfate, and magnesium oxide, wherein the at least one propellant is present in the container mixed with the composition or is present in the container separate from the composition; and (b) at least one diffuser disposed on the container and comprising:

at least three spray orifices with a spraying direction (Y), wherein axes of the at least three spray orifices are parallel to each other and parallel to the spraying direction (Y);

a delivery channel configured to receive the composition from the container; and feed channels that are inclined obliquely relative to the spraying direction (Y) and the delivery channel, the feed channels being configured to respectively provide the composition to the at least three spray orifices from the delivery channel.

2. The device according to claim 1, wherein the at least one propellant is present in the composition, and the at least one sebum-absorbing powder is present in an amount ranging from about 9.4% to 30% by weight, relative to the total weight of the composition.

3. The device according to claim 1, wherein the composition further comprises at least one $C_{2-4}$ monoalcohol.

4. The device according to claim 3, wherein the at least one propellant is present in the composition, and the at least one $C_{2-4}$ monoalcohol is present in an amount ranging from about 1% to about 70% by weight, relative to the total weight of the composition.

5. The device according to claim 1, wherein the at least one propellant is chosen from air, nitrogen, carbon dioxide, dimethyl ether, $C_{3-5}$ alkanes, 1,1-difluoroethane, and mixtures thereof.

6. The device according to claim 1, wherein the at least one propellant is present in the composition in an amount ranging from about 10% to about 90% by weight, relative to the total weight of the composition.

7. The device according to claim 1, wherein the composition further comprises at least one non-elastomeric silicone.

8. The device according to claim 7, wherein the at least one non-elastomeric silicone is chosen from silicone gums having a viscosity greater than $0.5 \times 10^{-3}$ m²/s (500 cSt).

9. The device according to claim 1, wherein the composition further comprises at least one fatty ester.

10. The device according to claim 1, wherein the composition further comprises at least one additive chosen from conditioning or fixing anionic, cationic, nonionic, amphoteric or zwitterionic polymers, fragrances, dyes, protective screening agents, acids, bases, nacres, and glitter flakes.

11. The device according to claim 1, wherein the at least three spray orifices are arranged at 120° relative to each other around the spraying direction (Y).

12. A process for the dry-washing and cosmetic treatment of keratin materials, comprising:

(I) spraying a composition from an aerosol device, comprising:

(a) a container comprising:

at least one propellant, and the a composition, the composition comprising:

from 8.6% to 30% by weight, based on the total weight of the composition and the at least one propellant, of at least one sebum absorbing powder chosen from modified starches having a sebum uptake of greater than or equal to 35 ml/100 g; and from 1% to 10% by weight, based on the total weight of the composition and the at least one propellant, of a styling powder comprising at least one water-insoluble mineral compound chosen from calcium carbonate, magnesium carbonate, alumina, barium sulfate, and magnesium oxide, wherein the at least one propellant is present in the container mixed with the composition or is present in the container separate from the composition; and (b) at least one diffuser disposed on the container and comprising:

at least three spray orifices with a spraying direction (Y), wherein axes of the at least three spray orifices are parallel to each other and parallel to the spraying direction (Y);

a delivery channel configured to receive the composition from the container; and feed channels that are inclined obliquely relative to the spraying direction (Y) and the delivery channel, the feed channels being configured to respectively provide the composition to the at least three spray orifices from the delivery channel;

(II) applying said composition to wet or dry hair; and (III) optionally, rinsing the hair after an optional leave-on time.

13. An aerosol device comprising:

(a) a container comprising:

at least one propellant, and a composition comprising:

from 8.6% to 30% by weight, based on the total weight of the composition and the at least one propellant, of at least one sebum-absorbing powder chosen from modified starches having a sebum uptake of greater than or equal to 35 ml/100 g; and from 1% to 10% by weight, based on the total weight of the composition and the at least one propellant, of a styling powder comprising at least one water-insoluble mineral compound chosen from calcium carbonate, magnesium carbonate, alumina, barium sulfate, and magnesium oxide; and at least one non-elastomeric silicone in an amount ranging from about 0.5% to about 5% by weight, relative to the total weight of the composition, wherein the at least one propellant is present in the composition and/or in the container, separate from the composition; and (b) at least one diffuser disposed on the container and comprising:

at least three spray orifices with a spraying direction (Y), wherein axes of the at least three spray orifices are parallel to each other and parallel to the spraying direction (Y);

a delivery channel configured to receive the composition from the container; and feed channels that are inclined obliquely relative to the spraying direction (Y) and the delivery channel, the feed channels being configured to respectively provide the composition to the at least three spray orifices from the delivery channel.

14. An aerosol device comprising:
(a) a container comprising:
  at least one propellant, and
  a composition comprising:
    from 9.4% to 30% by weight, based on the total weight of the composition and the at least one propellant, of at least one sebum-absorbing powder chosen from modified starches having a sebum uptake of greater than or equal to 35 ml/100 g;
    from 1% to 10% by weight, based on the total weight of the composition and the at least one propellant, of a styling powder comprising at least one water-insoluble mineral compound chosen from calcium carbonate, magnesium carbonate, alumina, barium sulfate, and magnesium oxide; and
  isopropyl myristate or palmitate,
    wherein the at least one propellant is present in the container mixed with composition or is present in the container, separate from the composition; and
(b) at least one diffuser comprising:
  at least three spray orifices with a spraying direction (Y), wherein axes of the at least three spray orifices are parallel to each other and parallel to the spraying direction (Y);
  a delivery channel configured to receive the composition from the container; and
  feed channels that are inclined obliquely relative to the spraying direction (Y) and the delivery channel, the feed channels being configured to respectively provide the composition to the at least three spray orifices from the delivery channel.

\* \* \* \* \*

UNITED STATES PATENT AND TRADEMARK OFFICE
CERTIFICATE OF CORRECTION

| | | |
|---|---|---|
| PATENT NO. | : 11,641,917 B2 | Page 1 of 1 |
| APPLICATION NO. | : 14/888013 | |
| DATED | : May 9, 2023 | |
| INVENTOR(S) | : Lionel Aubert et al. | |

It is certified that error appears in the above-identified patent and that said Letters Patent is hereby corrected as shown below:

In the Claims

Claim 12, Column 14, Line 7, delete "the a composition,".

Signed and Sealed this
Thirtieth Day of January, 2024

Katherine Kelly Vidal
*Director of the United States Patent and Trademark Office*